United States Patent
Budzik et al.

(10) Patent No.: US 9,643,916 B2
(45) Date of Patent: May 9, 2017

(54) LOW MOLECULAR WEIGHT CATIONIC LIPIDS FOR OLIGONUCLEOTIDE DELIVERY

(71) Applicant: SIRNA THERAPEUTICS, INC., Cambridge, MA (US)

(72) Inventors: Brian W. Budzik, Perkiomenville, PA (US); Steven L. Colletti, Princeton Junction, NJ (US); Jennifer R. Davis, Richboro, PA (US); Ivory D. Hills, Deerfield, MA (US); Darla Danile Seifried, Lansdale, PA (US); Matthew G. Stanton, Marlton, NJ (US)

(73) Assignee: SIRNA THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 15/077,447

(22) Filed: Mar. 22, 2016

(65) Prior Publication Data
US 2017/0050917 A1 Feb. 23, 2017

Related U.S. Application Data

(63) Continuation of application No. 14/711,246, filed on May 13, 2015, now Pat. No. 9,315,437, which is a continuation of application No. 14/265,029, filed on Apr. 29, 2014, now Pat. No. 9,062,021, which is a continuation of application No. 13/701,636, filed as application No. PCT/US2011/038490 on May 31, 2011, now Pat. No. 8,748,667.

(60) Provisional application No. 61/382,067, filed on Sep. 13, 2010, provisional application No. 61/351,373, filed on Jun. 4, 2010.

(51) Int. Cl.
*C07C 217/46* (2006.01)
*C07D 317/28* (2006.01)
*C07C 217/44* (2006.01)
*C07D 295/084* (2006.01)

(52) U.S. Cl.
CPC .......... *C07C 217/46* (2013.01); *C07C 217/44* (2013.01); *C07D 295/084* (2013.01); *C07D 317/28* (2013.01)

(58) Field of Classification Search
None
See application file for complete search history.

(56) References Cited

U.S. PATENT DOCUMENTS

| 6,060,455 | A | 5/2000 | Fernholz et al. |
| 8,748,667 | B2 | 6/2014 | Budzik et al. |
| 9,062,021 | B2 | 6/2015 | Budzik et al. |
| 2009/0285881 | A1 | 11/2009 | Dande et al. |
| 2010/0055168 | A1 | 3/2010 | Dande et al. |
| 2010/0063135 | A1 | 3/2010 | Dande et al. |
| 2010/0099738 | A1 | 4/2010 | Hansen et al. |

FOREIGN PATENT DOCUMENTS

WO 2009129385 10/2009

OTHER PUBLICATIONS

Database CAPLUS on STN, Acc. No. 1999:65895, Bissel et al., Langmuir (1999), 15(5), p. 1791-1795.
Semple et al. "Rational design of cationic lipids for siRNA delivery", Nat. Biotechnol, 28(2): 172-6; p. 713, Fig. 2C., Feb. 2010.

*Primary Examiner* — Brian J Davis
(74) *Attorney, Agent, or Firm* — Nixon Peabody LLP; David S. Resnick

(57) ABSTRACT

The instant invention provides for novel cationic lipids that can be used in combination with other lipid components such as cholesterol and PEG-lipids to form lipid nanoparticles with oligonucleotides. It is an object of the instant invention to provide a cationic lipid scaffold that demonstrates enhanced efficacy along with lower liver toxicity as a result of lower lipid levels in the liver. The present invention employs low molecular weight cationic lipids with one short lipid chain to enhance the efficiency and tolerability of in vivo delivery of siRNA.

6 Claims, 2 Drawing Sheets

```
                       SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)...(1)
<223> OTHER INFORMATION: 2'-deoxy
<220> FEATURE:
<221> NAME/KEY: misc_feature
<222> LOCATION: (2)...(2)
<223> OTHER INFORMATION: 2'-fluoro
<220> FEATURE:
<221> NAME/KEY: misc_feature
<222> LOCATION: (3)...(6)
<223> OTHER INFORMATION: 2'-deoxy
<220> FEATURE:
<221> NAME/KEY: misc_feature
<222> LOCATION: (7)...(8)
<223> OTHER INFORMATION: 2'-fluoro
<220> FEATURE:
<221> NAME/KEY: misc_feature
<222> LOCATION: (9)...(9)
<223> OTHER INFORMATION: 2'-deoxy
<220> FEATURE:
<221> NAME/KEY: misc_feature
<222> LOCATION: (10)...(10)
<223> OTHER INFORMATION: 2'-fluoro
<220> FEATURE:
<221> NAME/KEY: misc_feature
<222> LOCATION: (11)...(17)
<223> OTHER INFORMATION: 2'-deoxy
<220> FEATURE:
<221> NAME/KEY: misc_feature
<222> LOCATION: (18)...(18)
<223> OTHER INFORMATION: 2'-fluoro
<220> FEATURE:
<221> NAME/KEY: misc_feature
<222> LOCATION: (19)...(21)
<223> OTHER INFORMATION: 2'-deoxy

<400> SEQUENCE: 1
auaaggcuau gaagagauat t                                              21

<210> SEQ ID NO 2
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)...(3)
<223> OTHER INFORMATION: ribose
<220> FEATURE:
<221> NAME/KEY: misc_feature
<222> LOCATION: (4)...(9)
<223> OTHER INFORMATION: 2'-fluoro
<220> FEATURE:
<221> NAME/KEY: misc_feature
<222> LOCATION: (10)...(10)
```

```
<223> OTHER INFORMATION: 2'-o-methyl
<220> FEATURE:
<221> NAME/KEY: misc_feature
<222> LOCATION: (11)...(11)
<223> OTHER INFORMATION: 2'-fluoro
<220> FEATURE:
<221> NAME/KEY: misc_feature
<222> LOCATION: (12)...(13)
<223> OTHER INFORMATION: 2'-o-methyl
<220> FEATURE:
<221> NAME/KEY: misc_feature
<222> LOCATION: (14)...(17)
<223> OTHER INFORMATION: 2'-fluoro
<220> FEATURE:
<221> NAME/KEY: misc_feature
<222> LOCATION: (18)...(18)
<223> OTHER INFORMATION: 2'-o-methyl
<220> FEATURE:
<221> NAME/KEY: misc_feature
<222> LOCATION: (19)...(19)
<223> OTHER INFORMATION: 2'-fluoro
<220> FEATURE:
<221> NAME/KEY: misc_feature
<222> LOCATION: (20)...(21)
<223> OTHER INFORMATION: 2'-o-methyl

<400> SEQUENCE: 2
uaucucuuca uagccuuauu u                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)...(4)
<223> OTHER INFORMATION: 2'-fluoro
<220> FEATURE:
<221> NAME/KEY: misc_feature
<222> LOCATION: (5)...(6)
<223> OTHER INFORMATION: 2'-deoxy
<220> FEATURE:
<221> NAME/KEY: misc_feature
<222> LOCATION: (7)...(7)
<223> OTHER INFORMATION: 2'-fluoro
<220> FEATURE:
<221> NAME/KEY: misc_feature
<222> LOCATION: (8)...(9)
<223> OTHER INFORMATION: 2'-deoxy
<220> FEATURE:
<221> NAME/KEY: misc_feature
<222> LOCATION: (10)...(14)
<223> OTHER INFORMATION: 2'-fluoro
<220> FEATURE:
<221> NAME/KEY: misc_feature
<222> LOCATION: (15)...(18)
<223> OTHER INFORMATION: 2'-deoxy
<220> FEATURE:
<221> NAME/KEY: misc_feature
<222> LOCATION: (19)...(19)
<223> OTHER INFORMATION: 2'-fluoro
<220> FEATURE:
<221> NAME/KEY: misc_feature
<222> LOCATION: (20)...(21)
<223> OTHER INFORMATION: 2'-deoxy

<400> SEQUENCE: 3
cuuuaacaau uccugaaaut t                                              21
```

```
<210> SEQ ID NO 4
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: ribose
<220> FEATURE:
<221> NAME/KEY: misc_feature
<222> LOCATION: (4)..(5)
<223> OTHER INFORMATION: 2'-fluoro
<220> FEATURE:
<221> NAME/KEY: misc_feature
<222> LOCATION: (6)..(10)
<223> OTHER INFORMATION: 2'-O-methyl
<220> FEATURE:
<221> NAME/KEY: misc_feature
<222> LOCATION: (11)..(12)
<223> OTHER INFORMATION: 2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(15)
<223> OTHER INFORMATION: 2'-fluoro
<220> FEATURE:
<221> NAME/KEY: misc_feature
<222> LOCATION: (16)..(21)
<223> OTHER INFORMATION: 2'-O-methyl

<400> SEQUENCE: 4
auuucaggaa uuguuaaagu u                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified or unmodified as
      described for this sequence
<220> FEATURE:
<221> NAME/KEY: misc_feature
<222> LOCATION: (1)..(4)
<223> OTHER INFORMATION: 2'-O-methyl
<220> FEATURE:
<221> NAME/KEY: misc_feature
<222> LOCATION: (5)..(6)
<223> OTHER INFORMATION: 2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(9)
<223> OTHER INFORMATION: 2'-fluoro
<220> FEATURE:
<221> NAME/KEY: misc_feature
<222> LOCATION: (10)..(14)
<223> OTHER INFORMATION: 2'-O-methyl
<220> FEATURE:
<221> NAME/KEY: misc_feature
<222> LOCATION: (15)..(18)
<223> OTHER INFORMATION: 2'-fluoro
<220> FEATURE:
<221> NAME/KEY: misc_feature
<222> LOCATION: (19)..(19)
```

```
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 5
cuuuaacaau uccugaaaut t                                              21

<210> SEQ ID NO 6
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: ribose
<220> FEATURE:
<221> NAME/KEY: misc_feature
<222> LOCATION: (4)..(5)
<223> OTHER INFORMATION: 2'-O-methyl
<220> FEATURE:
<221> NAME/KEY: misc_feature
<222> LOCATION: (6)..(10)
<223> OTHER INFORMATION: 2'-fluoro
<220> FEATURE:
<221> NAME/KEY: misc_feature
<222> LOCATION: (11)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(19)
<223> OTHER INFORMATION: 2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (1)..(4)
<223> OTHER INFORMATION: phosphorothioate linkage
<220> FEATURE:
<221> NAME/KEY: misc_feature
<222> LOCATION: (20)..(21)
<223> OTHER INFORMATION: phosphorothioate linkage

<400> SEQUENCE: 6
auuucaggaa uuguuaaagu u                                              21
```

LOW MOLECULAR WEIGHT CATIONIC LIPIDS FOR OLIGONUCLEOTIDE DELIVERY

CROSS REFERENCE TO RELATED APPLICATIONS

This application is a Continuation of U.S. patent application Ser. No. 14/711,246, filed May 13, 2015, which is a Continuation of U.S. patent application Ser. No. 14/265,029 filed Apr. 29, 2014, now U.S. Pat. No. 9,062,021 issued Jun. 23, 2015, which is a Continuation of U.S. patent application Ser. No. 13/701,636 filed Dec. 3, 2012, now U.S. Pat. No. 8,748,667 issued Jun. 10, 2014, which is 371 National Phase Entry of International Patent Application No. PCT/US2011/038490 filed on May 31, 2011, and which claims benefit under 35 U.S.C. §119(e) of the U.S. Provisional Application No. 61/351,373, filed Jun. 4, 2010 and U.S. Provisional Application No. 61/382,067, filed Sep. 13, 2010, the contents of which are incorporated herein by reference in its entirety.

The sequence listing of the present application has been submitted electronically via EFS-Web as an ASCII formatted sequence listing with a file name "MRLMIS00035USPCT-SEQTXT-30NOV2012.txt", creation date Mar. 14, 2016 size of 5483 bytes. The sequence listing submitted via EFS-Web is part of the specification and is herein incorporated by reference in its entirety.

BACKGROUND OF THE INVENTION

The present invention relates to novel cationic lipids that can be used in combination with other lipid components such as cholesterol and PEG-lipids to form lipid nanoparticles with oligonucleotides, to facilitate the cellular uptake and endosomal escape, and to knockdown target mRNA both in vitro and in vivo.

Cationic lipids and the use of cationic lipids in lipid nanoparticles for the delivery of oligonucleotides, in particular siRNA and miRNA, have been previously disclosed. Lipid nanoparticles and use of lipid nanoparticles for the delivery of oligonucleotides, in particular siRNA and miRNA, has been previously disclosed. Oligonucleotides (including siRNA and miRNA) and the synthesis of oligonucleotides has been previously disclosed. (See US patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405 and WO2010/054406). See also Semple S. C. et al., Rational design of cationic lipids for siRNA delivery, Nature Biotechnology, published online 17 Jan. 2010; doi:10.1038/nbt.1602.

Other cationic lipids are disclosed in US patent applications: US 2009/0263407, US 2009/0285881, US 2010/0055168, US 2010/0055169, US 2010/0063135, US 2010/0076055, US 2010/0099738 and US 2010/0104629.

Traditional cationic lipids such as CLinDMA and DLinDMA have been employed for siRNA delivery to liver but suffer from non-optimal delivery efficiency along with liver toxicity at higher doses. It is an object of the instant invention to provide a cationic lipid scaffold that demonstrates enhanced efficacy along with lower liver toxicity as a result of lower lipid levels in the liver. The present invention employs low molecular weight cationic lipids with one short lipid chain to enhance the efficiency and tolerability of in vivo delivery of siRNA.

SUMMARY OF THE INVENTION

The instant invention provides for novel cationic lipids that can be used in combination with other lipid components such as cholesterol and PEG-lipids to form lipid nanoparticles with oligonucleotides. It is an object of the instant invention to provide a cationic lipid scaffold that demonstrates enhanced efficacy along with lower liver toxicity as a result of lower lipid levels in the liver. The present invention employs low molecular weight cationic lipids with one short lipid chain to enhance the efficiency and tolerability of in vivo delivery of siRNA.

DETAILED DESCRIPTION OF THE INVENTION

Figure 1:
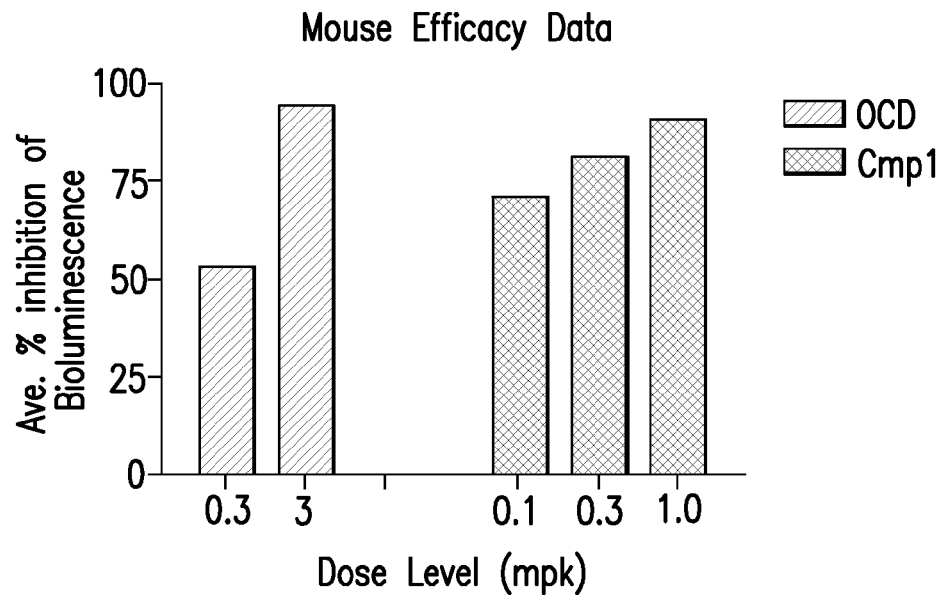
FIG. 1: LNP (Compound 1) efficacy in mice.

The various aspects and embodiments of the invention are directed to the utility of novel cationic lipids useful in lipid nanoparticles to deliver oligonucleotides, in particular, siRNA and miRNA, to any target gene. (See US patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405 and WO2010/054406). See also Semple S. C. et al., Rational design of cationic lipids for siRNA delivery, Nature Biotechnology, published online 17 Jan. 2010; doi:10.1038/nbt.1602.

The cationic lipids of the instant invention are useful components in a lipid nanoparticle for the delivery of oligonucleotides, specifically siRNA and miRNA.

In a first embodiment of this invention, the cationic lipids are illustrated by the Formula A:

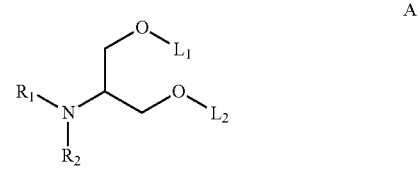

A wherein:

$R^1$ and $R^2$ are independently selected from H, $(C_1-C_6)$ alkyl, heterocyclyl, and polyamine, wherein said alkyl, heterocyclyl and polyamine are optionally substituted with one to three substituents selected from R', or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one to three substituents selected from R';

R' is independently selected from halogen, R", OR", SR", CN, $CO_2R"$ or $CON(R")_2$;

R'' is independently selected from H and $(C_1-C_6)$alkyl, wherein said alkyl is optionally substituted with halogen and OH;

$L_1$ is selected from $C_4-C_{22}$ alkyl and $C_4-C_{22}$ alkenyl, said alkyl and alkenyl are optionally substituted with one or more substituents selected from R'; and $L_2$ is selected from $C_3-C_{13}$ alkyl and $C_3-C_{13}$ alkenyl, said alkyl and alkenyl are optionally substituted with one or more substituents selected from R';

or any pharmaceutically acceptable salt or stereoisomer thereof.

In a second embodiment, the invention features a compound having Formula A, wherein:

$R^1$ and $R^2$ are each methyl;

$L_1$ is selected from $C_4-C_{22}$ alkyl and $C_4-C_{22}$ alkenyl; and $L_2$ is selected from $C_3-C_{13}$ alkyl and $C_3-C_{13}$ alkenyl;

or any pharmaceutically acceptable salt or stereoisomer thereof.

Specific cationic lipids are:

R-N,N-dimethyl-1-[(9Z,12Z)-octadeca-9,12-dien-1-yloxy]-3-(octyloxy)propan-2-amine (Compound 2);

S-N,N-dimethyl-1-[(9Z,12Z)-octadeca-9,12-dien-1-yloxy]-3-(octyloxy)propan-2-amine (Compound 1);

1-{2-[(9Z,12Z)-octadeca-9,12-dien-1-yloxy]-1-[(octyloxy)methyl]ethyl}pyrrolidine (Compound 3);

(2S)-N,N-dimethyl-1-[(9Z,12Z)-octadeca-9,12-dien-1-yloxy]-3-[(5Z)-oct-5-en-1-yloxy]propan-2-amine (Compound 4);

1-{2-[(9Z,12Z)-octadeca-9,12-dien-1-yloxy]-1-[(octyloxy)methyl]ethyl}azetidine (Compound 5);

(2S)-1-(hexyloxy)-N,N-dimethyl-3-[(9Z,12Z)-octadeca-9,12-dien-1-yloxy]propan-2-amine (Compound 6);

(2S)-1-(heptyloxy)-N,N-dimethyl-3-[(9Z,12Z)-octadeca-9,12-dien-1-yloxy]propan-2-amine (Compound 7);

N,N-dimethyl-1-(nonyloxy)-3-[(9Z,12Z)-octadeca-9,12-dien-1-yloxy]propan-2-amine (Compound 8);

N,N-dimethyl-1-[(9Z)-octadec-9-en-1-yloxy]-3-(octyloxy)propan-2-amine (Compound 9);

(2S)-N,N-dimethyl-1-[(6Z,9Z,12Z)-octadeca-6,9,12-trien-1-yloxy]-3-(octyloxy)propan-2-amine (Compound 10);

(2S)-1-[(11Z,14Z)-icosa-11,14-dien-1-yloxy]-N,N-dimethyl-3-(pentyloxy)propan-2-amine (Compound 11);

(2S)-1-(hexyloxy)-3-[(11Z,14Z)-icosa-11,14-dien-1-yloxy]-N,N-dimethylpropan-2-amine (Compound 12);

1-[(11Z,14Z)-icosa-11,14-dien-1-yloxy]-N,N-dimethyl-3-(octyloxy)propan-2-amine (Compound 13);

1-[(13Z,16Z)-docosa-13,16-dien-1-yloxy]-N,N-dimethyl-3-(octyloxy)propan-2-amine (Compound 14);

(2S)-1-[(13Z,16Z)-docosa-13,16-dien-1-yloxy]-3-(hexyloxy)-N,N-dimethylpropan-2-amine (Compound 15);

(2S)-1-[(13Z)-docos-13-en-1-yloxy]-3-(hexyloxy)-N,N-dimethylpropan-2-amine (Compound 16);

1-[(13Z)-docos-13-en-1-yloxy]-N,N-dimethyl-3-(octyloxy)propan-2-amine (Compound 17);

1-[(9Z)-hexadec-9-en-1-yloxy]-N,N-dimethyl-3-(octyloxy)propan-2-amine (Compound 18);

(2R)-N,N-dimethyl-1-[(1-methyloctyl)oxy]-3-[(9Z,12Z)-octadeca-9,12-dien-1-yloxy]propan-2-amine (Compound 19);

(2R)-1-[(3,7-dimethyloctyl)oxy]-N,N-dimethyl-3-[(9Z,12Z)-octadeca-9,12-dien-1-yloxy]propan-2-amine (Compound 20);

N,N-dimethyl-1-(octyloxy)-3-({8-[(1S,2S)-2-{[(1R,2R)-2-pentylcyclopropyl]methyl}cyclopropyl]octyl}oxy)propan-2-amine (Compound 21); and N,N-dimethyl-1-{[8-(2-octylcyclopropyl)octyl]oxy}-3-(octyloxy)propan-2-amine (Compound 22);

or any pharmaceutically acceptable salt or stereoisomer thereof.

In another embodiment, the cationic lipids disclosed are useful in the preparation of lipid nanoparticles.

In another embodiment, the cationic lipids disclosed are useful components in a lipid nanoparticle for the delivery of oligonucleotides.

In another embodiment, the cationic lipids disclosed are useful components in a lipid nanoparticle for the delivery of siRNA and miRNA.

In another embodiment, the cationic lipids disclosed are useful components in a lipid nanoparticle for the delivery of siRNA.

The cationic lipids of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the cationic lipids disclosed herein may exist as tautomers and both tautomeric forms are intended to be encompassed by the scope of the invention, even though only one tautomeric structure is depicted.

It is understood that substituents and substitution patterns on the cationic lipids of the instant invention can be selected by one of ordinary skill in the art to provide cationic lipids that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

It is understood that one or more Si atoms can be incorporated into the cationic lipids of the instant invention by one of ordinary skill in the art to provide cationic lipids that are chemically stable and that can be readily synthesized by techniques known in the art from readily available starting materials.

In the compounds of Formula A, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula A. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula A can be prepared without undue experimentation by conventional techniques well known to those skilled in the art or by processes analogous to those described in the Scheme and Examples herein using appropriate isotopically-enriched reagents and/or intermediates.

As used herein, "alkyl" means a straight chain, cyclic or branched saturated aliphatic hydrocarbon having the specified number of carbon atoms.

As used herein, "alkenyl" means a straight chain, cyclic or branched unsaturated aliphatic hydrocarbon having the specified number of carbon atoms including but not limited to diene, triene and tetraene unsaturated aliphatic hydrocarbons.

Examples of a cyclic "alkyl" or "alkenyl" are:

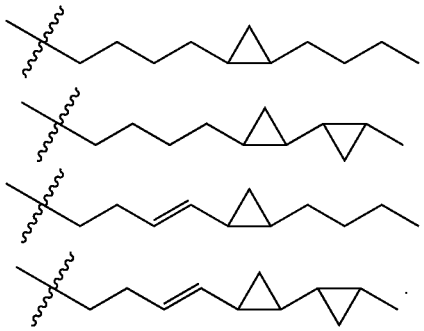

As used herein, "heterocyclyl" or "heterocycle" means a 4- to 10-membered aromatic or nonaromatic heterocycle containing from 1 to 4 heteroatoms selected from the group consisting of O, N and S, and includes bicyclic groups. "Heterocyclyl" therefore includes, the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof all of which are optionally substituted with one to three substituents selected from R".

As used herein, "polyamine" means compounds having two or more amino groups. Examples include putrescine, cadaverine, spermidine, and spermine.

As used herein, "halogen" means Br, Cl, F and I.

In an embodiment of Formula A, $R^1$ and $R^2$ are independently selected from H and $(C_1-C_6)$alkyl, wherein said alkyl is optionally substituted with one to three substituents selected from R', or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocycle heterocycle is optionally substituted with one to three substituents selected from R'.

In an embodiment of Formula A, $R^1$ and $R^2$ are independently selected from H, methyl, ethyl and propyl, wherein said methyl, ethyl and propyl are optionally substituted with one to three substituents selected from R', or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocycle heterocycle is optionally substituted with one to three substituents selected from R'.

In an embodiment of Formula A, $R^1$ and $R^2$ are independently selected from H, methyl, ethyl and propyl.

In an embodiment of Formula A, $R^1$ and $R^2$ are each methyl.

In an embodiment of Formula A, R' is R".

In an embodiment of Formula A, R" is independently selected from H, methyl, ethyl and propyl, wherein said methyl, ethyl and propyl are optionally substituted with one or more halogen and OH.

In an embodiment of Formula A, R" is independently selected from H, methyl, ethyl and propyl.

In an embodiment of Formula A, $L_1$ is selected from $C_4-C_{22}$ alkyl and $C_4-C_{22}$ alkenyl, which are optionally substituted with halogen and OH.

In an embodiment of Formula A, $L_1$ is selected from $C_4-C_{22}$ alkyl and $C_4-C_{22}$ alkenyl.

In an embodiment of Formula A, $L_1$ is selected from $C_4-C_{22}$ alkenyl.

In an embodiment of Formula A, $L_1$ is selected from $C_{12}-C_{22}$ alkenyl.

In an embodiment of Formula A, $L_1$ is $C_{18}$ alkenyl.

In an embodiment of Formula A, $L_1$ is:

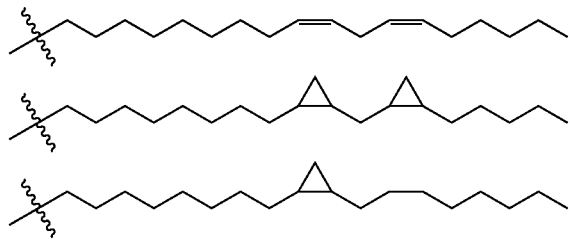

In an embodiment of Formula A, $L_1$ is:

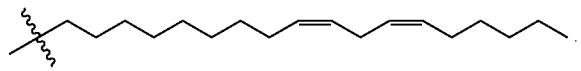

In an embodiment of Formula A, $L_2$ is selected from $C_3-C_{13}$ alkyl and $C_3-C_{13}$ alkenyl, which are optionally substituted with halogen and OH.

In an embodiment of Formula A, $L_2$ is selected from $C_3-C_9$ alkyl and $C_3-C_9$ alkenyl, which are optionally substituted with halogen and OH.

In an embodiment of Formula A, $L_2$ is selected from $C_3-C_8$ alkyl and $C_3-C_8$ alkenyl, which are optionally substituted with halogen and OH.

In an embodiment of Formula A, $L_2$ is selected from $C_3-C_{13}$ alkyl and $C_3-C_{13}$ alkenyl.

In an embodiment of Formula A, $L_2$ is selected from $C_3-C_9$ alkyl and $C_3-C_9$ alkenyl.

In an embodiment of Formula A, $L_2$ is selected from $C_3-C_8$ alkyl and $C_3-C_8$ alkenyl.

In an embodiment of Formula A, $L_2$ is $C_3-C_{13}$ alkyl.

In an embodiment of Formula A, $L_2$ is $C_3-C_9$ alkyl.

In an embodiment of Formula A, $L_2$ is $C_3-C_8$ alkyl.

In an embodiment of Formula A, $L_2$ is $C_8$ alkyl.

In an embodiment of Formula A, "heterocyclyl" is pyrolidine, piperidine, morpholine, imidazole or piperazine.

In an embodiment of Formula A, "monocyclic heterocyclyl" is pyrolidine, piperidine, morpholine, imidazole or piperazine.

In an embodiment of Formula A, "polyamine" is putrescine, cadaverine, spermidine or spermine.

In an embodiment, "alkyl" is a straight chain saturated aliphatic hydrocarbon having the specified number of carbon atoms.

In an embodiment, "alkenyl" is a straight chain unsaturated aliphatic hydrocarbon having the specified number of carbon atoms.

Included in the instant invention is the free form of cationic lipids of Formula A, as well as the pharmaceutically acceptable salts and stereoisomers thereof. Some of the isolated specific cationic lipids exemplified herein are the protonated salts of amine cationic lipids. The term "free form" refers to the amine cationic lipids in non-salt form. The encompassed pharmaceutically acceptable salts not only include the isolated salts exemplified for the specific cationic lipids described herein, but also all the typical pharmaceutically acceptable salts of the free form of cationic lipids of Formula A. The free form of the specific salt cationic lipids described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant cationic lipids can be synthesized from the cationic lipids of this invention which contain a basic or acidic moiety by conventional chemical methods. Generally, the salts of the basic cationic lipids are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the cationic lipids of this invention include the conventional non-toxic salts of the cationic lipids of this invention as formed by reacting a basic instant cationic lipids with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the cationic lipids of the present invention are acidic, suitable "pharmaceutically acceptable salts" refers to salts prepared form pharmaceutically acceptable Don-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the cationic lipids of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

EXAMPLES

Examples provided are intended to assist in a further understanding of the invention. Particular materials employed, species and conditions are intended to be further illustrative of the invention and not limitative of the reasonable scope thereof. The reagents utilized in synthesizing the cationic lipids are either commercially available or are readily prepared by one of ordinary skill in the art.

Synthesis of the novel cationic lipids is a linear process starting epichlorohydrin (i). Reaction of epichlorohydrin with lipid alcohol gives intermediate epoxide ii. Lewis acid epoxide opening with the second lipid alcohol affords secondary alcohol iii. Triflate formation and amine substitution gives final products of type iv.

GENERAL SCHEME 1

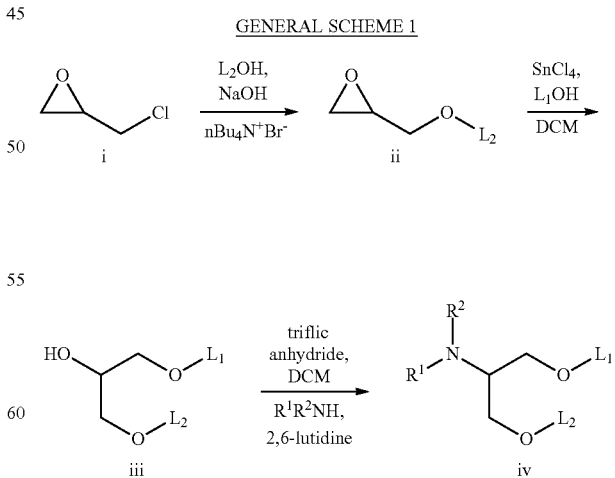

Synthesis of intermediate cyclopropyl analogs (vi) was conducted by Simmons-Smith cyclopropanation of olefins of type v.

GENERAL SCHEME 2

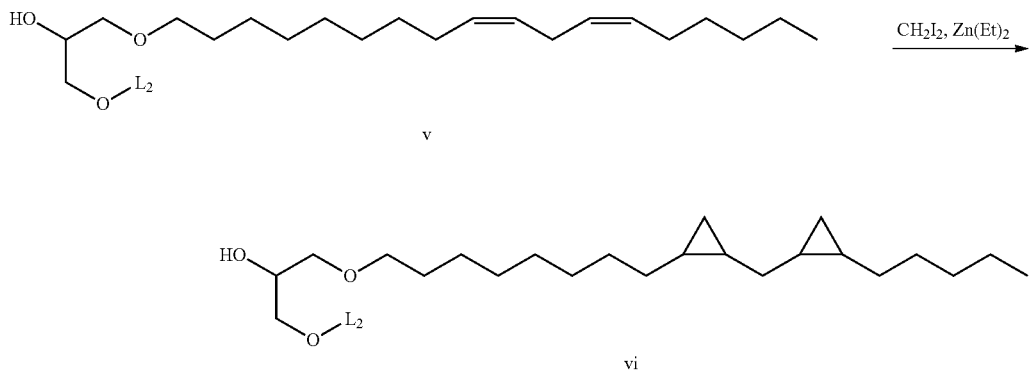

SCHEME 1
S-N,N-dimethyl-1-[(9Z,12Z)-octadeca-9,12-dien-1-yloxy]-3-(octyloxy)propan-2-amine (Compound 1)

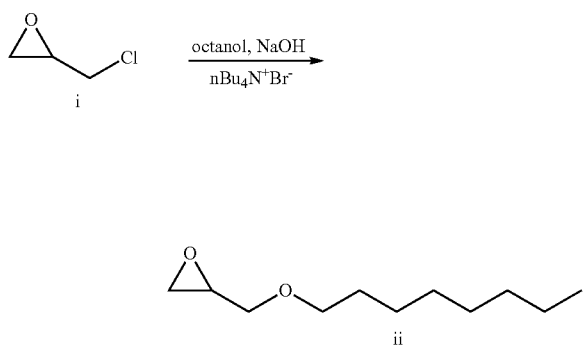

A solution of octanol (1.5 mol, 195 g), tetrabutyl ammonium bromide (75 mmol, 24.1 g) and sodium hydroxide (2.4 mol, 96 g) was cooled to 3 C and R-epichlorohydrin was added via dropping funnel. The mixture was stirred at 3 C for 6 hours and then allowed to warm to ambient temperature for 16 hours. The reaction was partitioned between hexanes and aqueous saturated sodium bicarbonate. The organics were washed with water (2×625 mL) and brine (625 mL) and evaporated in vacuo. The crude oil was purified by flash chromatography (silica, 0-20% ethyl acetate/heptane) to give 236 g (85%) of one of the enantiomers of 2-[(octyloxy)methyl]oxirane as a clear oil. $^1$H NMR (400 MHz, CDCl3): δ 3.68 (m, 1H), 3.45 (m, 2H), 3.38 (m, 1H), 3.16 (m, 1H), 2.78 (m, 1H), 2.59 (m, 1H), 1.58 (m, 2H), 1.30 (m, 10H), 0.83 (m, 3H).

The product of this reaction was first assigned the 2R stereochemistry, which would be obtained via a SN2 mechanism at the carbon bearing the halide atom with no change at the asymmetric carbon centre.

However, subsequent studies (experiments on the reaction of lineolyl alcohol with S-epichlorohydrin), under conditions described, Lewis acid conditions and in conjunction with vibrational circular dichroism (VCD), a valid spectroscopic method for determining absolute configuration of chiral molecules (R. K. Dukor and L. A. Nafie, in *Encyclopedia of Analytical Chemistry: Instrumentation and Applications*, Ed. R. A. Meyers (Wiley, Chichester, 2000) 662-676) have revealed the reaction occurred via a SN2' mechanism ie reaction at the terminal carbon of the epoxide leading to subsequent ring opening, followed by an in situ ring closing step that leads to inversion of stereochemistry at the asymmetric carbon.

As a result of these studies, the product from this reaction was reassigned the 2S stereochemistry: (2S)-[(octyloxy)methyl]oxirane.

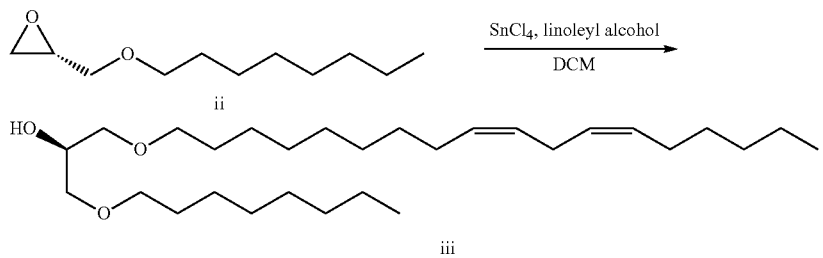

A solution of epoxide (3.86 g, 20.7 mmol) and linoleyl alcohol (6.6 g, 24.8 mmol) in dichloromethane (100 mL) was treated with tin tetrachloride (4.44 g, 2.0 mmol) at ambient temperature. After stirring for 3 hours, the reaction was quenched with brine and partitioned between brine and dichloromethane. The organics were dried over sodium sulfate, filtered and evaporated in vacuo. The crude oil was purified by flash chromatography (silica, 2-5% acetone/hexanes) to give 5.85 g (62%) of R-1-[(9Z,12Z)-octadeca-9,12-dien-1-yloxy]-3-(octyloxy)propan-2-ol as a clear oil. $^1$H NMR (400 MHz, CDCl3): δ 5.38 (m, 4H), 3.93 (m, 1H), 3.49 (m, 8H), 2.79 (m, 2H), 2.45 (m, 1H), 2.06 (m, 4H), 1.58 (m, 6H), 1.30 (m, 26H), 0.89 (m, 6H).

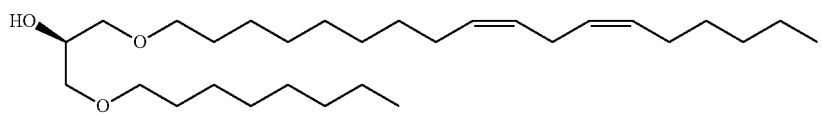

iii

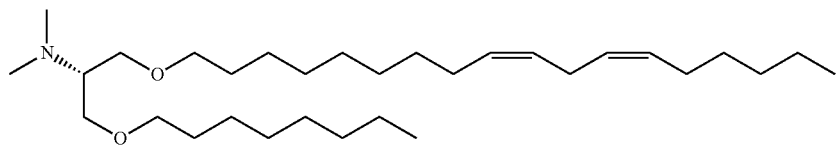

1

Compound iii (5.08 g, 11.2 mmol) was dissolved into dichloromethane (100 ml) and treated with 2,6-lutidine (1.44 g, 13.5 mmol). Triflic anhydride (3.8 g, 13.5 mmol) was added dropwise into the reaction system at 0° C. After 2.5 hours, the reaction was cannulated into a cold solution of dimethylamine (39.3 mmol) in dichloromethane (85 mL). After 2 hours at 0 C, the reaction was quenched with saturated sodium bicarbonate solution and partitioned between water/dichloromethane. The organics were dried over magnesium sulfate, filtered and evaporated in vacuo. The crude oil was purified by flash chromatography (silica, 0-30% ethyl acetate/hexanes) to give 3.66 g (65%) of S-N,N-dimethyl-1-[(9Z,12Z)-octadeca-9,12-dien-1-yloxy]-3-(octyloxy)propan-2-amine as an amber oil. $^1$H NMR (400 MHz, CDCl3): δ 5.38 (m, 4H), 3.52 (m, 4H), 3.40 (m, 4H), 2.79 (m, 3H), 2.40 (s, 6H), 2.05 (m, 4H), 1.58 (m, 4H), 1.30 (m, 26H), 0.89 (m, 6H). HRMS: cal'd—480.4775. found—480.4769.

Compound 2 is a novel cationic lipid and was prepared according to the General Scheme 1 and Scheme 1 above, starting with S-epichlorohydrin.

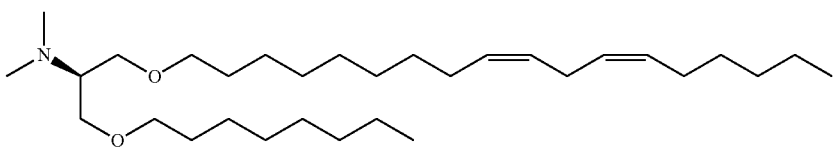 [SMILES: CCCCC/C=C\C/C=C\CCCCCCCCOC[C@@H](COCCCCCCCC)N(C)C]

Compound 2

R-N,N-dimethyl-1-[(9Z,12Z)-octadeca-9,12-dien-1-yloxy]-3-(octyloxy)propan-2-amine (Compound 2)

$^1$H NMR (400 MHz, CDCl3): δ 5.38 (m, 4H), 3.52 (m, 4H), 3.40 (m, 4H), 2.79 (m, 3H), 2.40 (s, 6H), 2.05 (m, 4H), 1.58 (m, 4H), 1.30 (m, 26H), 0.89 (m, 6H).

Compounds 3-20 were prepared in a manner analogous to that described for Compound 1 according to General Scheme 1.

| Compound | Name | Structure | HRMS/LCMS (M + H) |
|---|---|---|---|
| 3 | 1-{2-[(9Z,12Z)-octadeca-9,12-dien-1-yloxy]-1-[(octyloxy)-methyl]-ethyl}-pyrrolidine | 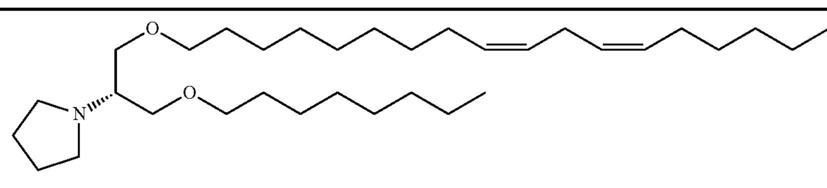 | C33H63NO2 [M + H] calc 506.5 obs 506.7 |
| 4 | (2S)-N,N-dimethyl-1-[(9Z,12Z)-octadeca-9,12-dien-1-yloxy]-3-[(5Z)-oct-5-en-1-yloxy]propan-2-amine | 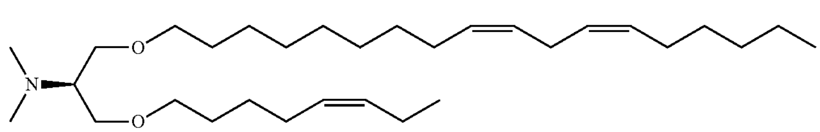 [SMILES: CC/C=C\CCCCOC[C@H](COCCCCCCCC/C=C\C/C=C\CCCCC)N(C)C] | C31H59NO2 [M + H] calc 478.5 obs 478.5 |

-continued

| Compound | Name | Structure | HRMS/LCMS (M + H) |
|---|---|---|---|
| 5 | 1-{2-[(9Z,12Z)-octadeca-9,12-dien-1-yloxy]-1-[(octyloxy)-methyl]-ethyl}azetidine | 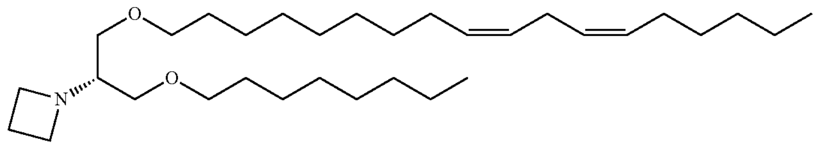 [SMILES: CCCCC/C=C\C/C=C\CCCCCCCCOC[C@H](COCCCCCCCC)N1CCC1] | C32H61NO2 [M + H] calc 492.5 obs 492.7 |
| 6 | (2S)-1-(hexyloxy)-N,N-dimethyl-3-[(9Z,12Z)-octadeca-9,12-dien-1-yloxy]propan-2-amine | 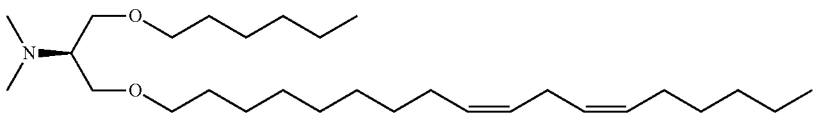 [SMILES: CCCCC/C=C\C/C=C\CCCCCCCCOC[C@H](COCCCCCC)N(C)C] | C29H57NO2 [M + H] calc 452.4 obs 452.4 |
| 7 | (2S)-1-(heptyloxy)-N,N-dimethyl-3-[(9Z,12Z)-octadeca-9,12-dien-1-yloxy]propan-2-amine | 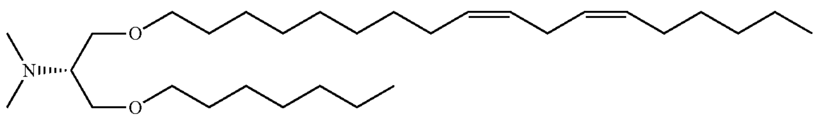 [SMILES: CCCCC/C=C\C/C=C\CCCCCCCCOC[C@H](COCCCCCCC)N(C)C] | C30H59NO2 [M + H] calc 466.5 obs 466.5 |
| 8 | N,N-dimethyl-1-(nonyloxy)-3-[(9Z,12Z)-octadeca-9,12-dien-1-yloxy]propan-2-amine | 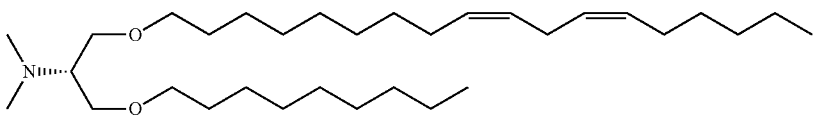 [SMILES: CCCCC/C=C\C/C=C\CCCCCCCCOC[C@H](COCCCCCCCCC)N(C)C] | C32H63NO2 [M + H] calc 494.5 obs 494.5 |
| 9 | N,N-dimethyl-1-[(9Z)-octadec-9-en-1-yloxy]-3-(octyloxy)-propan-2-amine | 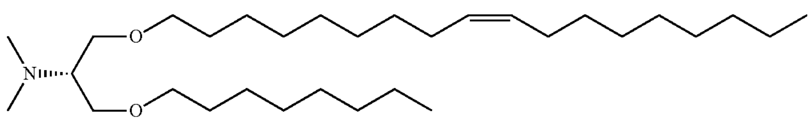 [SMILES: CCCCCCCC/C=C\CCCCCCCCOC[C@H](COCCCCCCCC)N(C)C] | C31H63NO2 [M + H] calc 482.5 obs 482.5 |
| 10 | (2S)-N,N-dimethyl-1-[(6Z,9Z,12Z)-octadeca-6,9,12-trien-1-yloxy]-3-(octyloxy)-propan-2-amine | 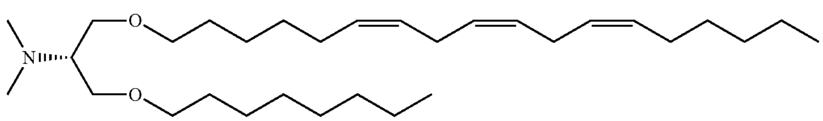 [SMILES: CCCCC/C=C\C/C=C\C/C=C\CCCCCOC[C@H](COCCCCCCCC)N(C)C] | C31H59NO2 [M + H] calc 478.5 obs 478.5 |
| 11 | (2S)-1-[(11Z,14Z)-icosa-11,14-dien-1-yloxy]-N,N-dimethyl-3-(pentyloxy)-propan-2-amine | 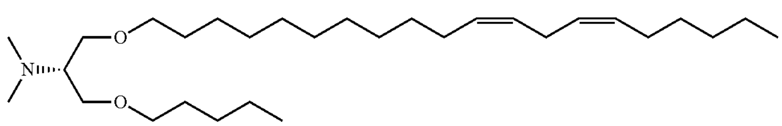 [SMILES: CCCCC/C=C\C/C=C\CCCCCCCCCCOC[C@H](COCCCCC)N(C)C] | C30H59NO2 [M + H] calc 466.5 obs 466.5 |
| 12 | (2S)-1-(hexyloxy)-3-[(11Z,14Z)-icosa-11,14-dien-1-yloxy]-N,N-dimethyl-propan-2-amine | 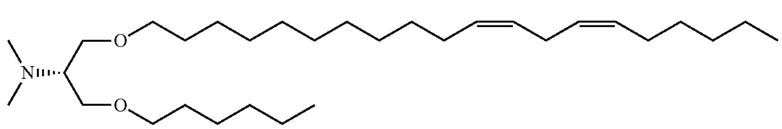 [SMILES: CCCCC/C=C\C/C=C\CCCCCCCCCCOC[C@H](COCCCCCC)N(C)C] | C31H61NO2 [M + H] calc 480.5 obs 480.5 |
| 13 | 1-[(11Z,14Z)-icosa-11,14-dien-1-yloxy]-N,N-dimethyl-3-(octyloxy)-propan-2-amine | 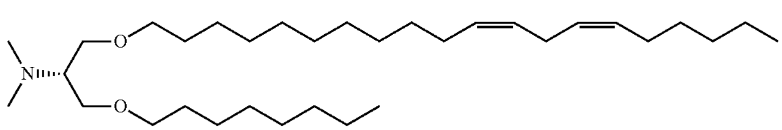 [SMILES: CCCCC/C=C\C/C=C\CCCCCCCCCCOC[C@H](COCCCCCCCC)N(C)C] | C33H65NO2 [M + H] calc 508.5 obs 508.5 |

-continued

| Compound | Name | Structure | HRMS/LCMS (M + H) |
|---|---|---|---|
| 14 | 1-[(13Z,16Z)-docosa-13,16-dien-1-yloxy]-N,N-dimethyl-3-(octyloxy)-propan-2-amine | 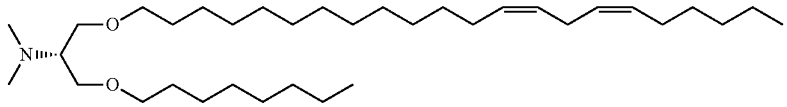 [SMILES: CCCCC/C=C\C/C=C\CCCCCCCCCCCCOC[C@H](COCCCCCCCC)N(C)C] | C35H69NO2 [M + H] calc 536.5 obs 536.5 |
| 15 | (2S)-1-[(13Z,16Z)-docosa-13,16-dien-1-yloxy]-3-(hexyloxy)-N,N-dimethyl-propan-2-amine | 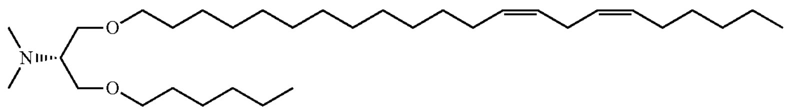 [SMILES: CCCCC/C=C\C/C=C\CCCCCCCCCCCCOC[C@H](COCCCCCC)N(C)C] | C33H65NO2 [M + H] calc 508.5 obs 508.5 |
| 16 | (2S)-1-[(13Z)-docos-13-en-1-yloxy]-3-(hexyloxy)-N,N-dimethyl-propan-2-amine | 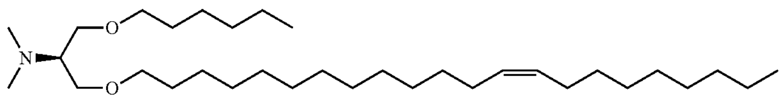 [SMILES: CCCCCCCC/C=C\CCCCCCCCCCCCOC[C@H](COCCCCCC)N(C)C] | C33H67NO2 [M + H] calc 510.5 obs 510.5 |
| 17 | 1-[(13Z)-docos-13-en-1-yloxy]-N,N-dimethyl-3-(octyloxy)-propan-2-amine | 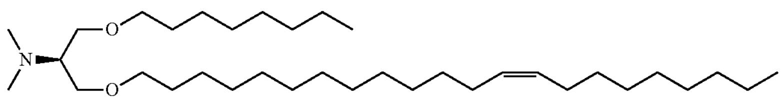 [SMILES: CCCCCCCC/C=C\CCCCCCCCCCCCOC[C@H](COCCCCCCCC)N(C)C] | C35H71NO2 [M + H] calc 538.6 obs 538.6 |
| 18 | 1-[(9Z)-hexadec-9-en-1-yloxy]-N,N-dimethyl-3-(octyloxy)-propan-2-amine | 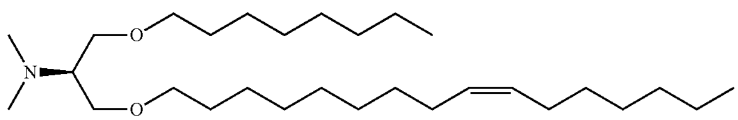 [SMILES: CCCCCC/C=C\CCCCCCCCOC[C@H](COCCCCCCCC)N(C)C] | C29H59NO2 [M + H] calc 454.5 obs 454.5 |
| 19 | (2R)-N,N-dimethyl-1-[(1-methyl-octyl)oxy]-3-[(9Z,12Z)-octadeca-9,12-dien-1-yloxy]propan-2-amine | 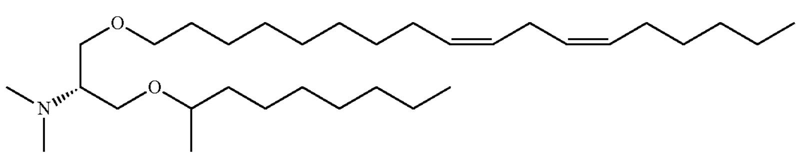 [SMILES: CCCCC/C=C\C/C=C\CCCCCCCCOC[C@H](COC(C)CCCCCCC)N(C)C] | C32H63NO2 [M + H] calc 494.5 obs 494.7 |
| 20 | (2R)-1-[(3,7-dimethyl-octyl)oxy]-N,N-dimethyl-3-[(9Z,12Z)-octadeca-9,12-dien-1-yloxy]propan-2-amine | 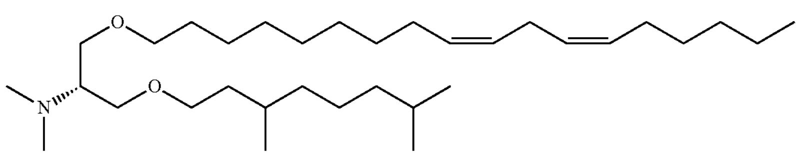 [SMILES: CCCCC/C=C\C/C=C\CCCCCCCCOC[C@H](COCCC(C)CCCC(C)C)N(C)C] | C33H65NO2 [M + H] calc 508.5 obs 508.5 |

SCHEME 2
N,N-dimethyl-1-(octyloxy)-3-({8-[(1S,2S)-2-{[(1R,2R)-2-pentylcyclopropyl]methyl}cyclopropyl]octyl}oxy)propan-2-amine (Compound 21)

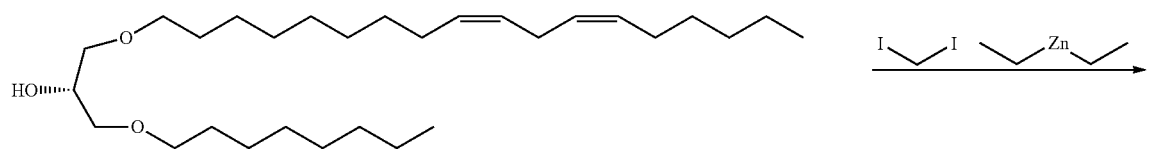

v

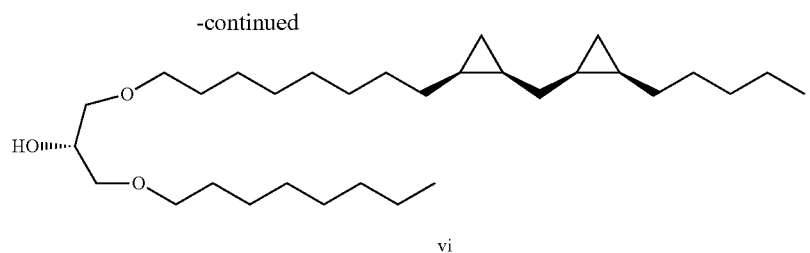

vi

A solution of 1-[(9Z,12Z)-octadeca-9,12-dien-1-yloxy]-3-(octyloxy)propan-2-ol in DCM (166 ml) in a 1 L flask under nitrogen was cooled in an ice/IPA bath (−15° C.) and then 1 M diethylzinc in hexane (199 ml, 199 mmol) added, followed by diiodomethane (24.05 ml, 298 mmol). The mixture was allowed to stir in the cooling bath overnight to gradually come up to room temperature. Reaction was quenched by addition of excess saturated ammonium chloride. Washed reaction into 2 L separatory funnel with hexane and water and added excess hexane, shook vigorously. Discarded lower aqueous layer, dried organic layer with sodium sulfate and evaporated to 1-(octyloxy)-3-[(8-{2-[(2-pentylcyclopropyl)methyl]cyclopropyl}octyl)oxy]propan-2-ol (15.5 g, 32.2 mmol, 97% yield) as a yellow oil. Material was used with no further purification. MS (ESI): 481 [M+H]+.

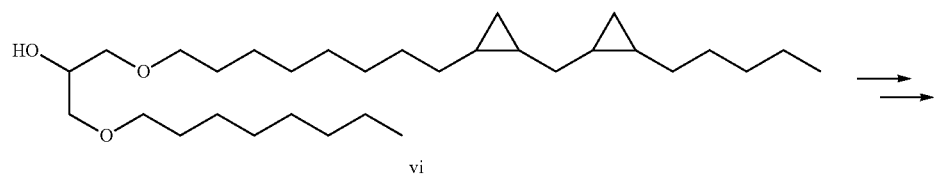

vi

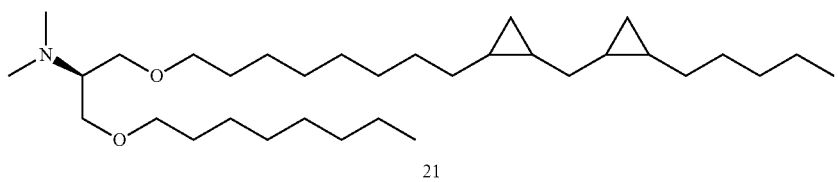

21

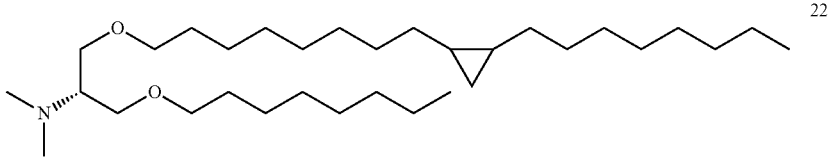 [SMILES: CCCCCCCCOC[C@@H](COCCCCCCCCC1CC1CCCCCCCC)N(C)C]

22

Conversion of alcohol vi to final compound 21 was accomplished as described for Compound 1. C33H65NO2 [M+H], calc 508.5, obs 508.5.

N,N-dimethyl-1-{[8-(2-octylcyclopropyl)octyl]oxy}-3-(octyloxy)propan-2-amine (Compound 22) was prepared in a manner analogous to that described for compound 21. C32H65NO2 [M+H], calc 496.5, obs 496.5.

Compound 23 is DLinDMA as described in *J. Controlled Release*, 2005, 107, 276-287, US 2006/0083780 A1, and US 2006/0008910 A1.

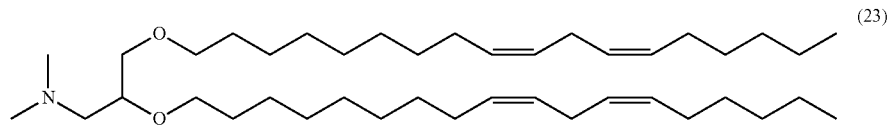 [SMILES: CCCCC/C=C\C/C=C\CCCCCCCCOCC(CN(C)C)OCCCCCCCC/C=C\C/C=C\CCCCC]

(23)

Compound 24 is DLinKC2DMA as described in *Nature Biotechnology*, 2010, 28, 172-176, WO 2010/042877 A1, WO 2010/048536 A2, WO 2010/088537 A2, and WO 2009/127060 A1.

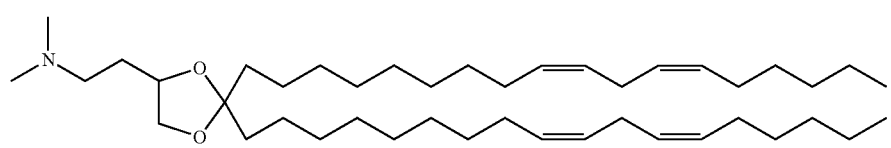

(24)

LNP Compositions

The following lipid nanoparticle compositions (LNPs) of the instant invention are useful for the delivery of oligonucleotides, specifically siRNA and miRNA:
Cationic Lipid/Cholesterol/PEG-DMG 56.6/38/5.4;
Cationic Lipid/Cholesterol/PEG-DMG 60/38/2;
Cationic Lipid/Cholesterol/PEG-DMG 67.3/29/3.7;
Cationic Lipid/Cholesterol/PEG-DMG 49.3/47/3.7;
Cationic Lipid/Cholesterol/PEG-DMG 50.3/44.3/50.4;
Cationic Lipid/Cholesterol/PEG-C-DMA/DSPC 40/48/2/10;
Cationic Lipid/Cholesterol/PEG-DMG/DSPC 40/48/2/10; and
Cationic Lipid/Cholesterol/PEG-DMG/DSPC 58/30/2/10.

The synthesis and use of LNPs are known. (See US patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405 and WO2010/054406). See also Semple S. C. et al., Rational design of cationic lipids for siRNA delivery, Nature Biotechnology, published online 17 Jan. 2010; doi:10.1038/nbt.1602.

LNP Process Description:

The Lipid Nano-Particles (LNP) are prepared by an impinging jet process. The particles are formed by mixing lipids dissolved in alcohol with siRNA dissolved in a citrate buffer. The mixing ratio of lipids to siRNA are targeted at 45-55% lipid and 65-45% siRNA. The lipid solution contains a novel cationic lipid of the instant invention, a helper lipid (cholesterol), PEG (e.g. PEG-C-DMA, PEG-DMG) lipid, and DSPC at a concentration of 5-15 mg/mL with a target of 9-12 mg/mL in an alcohol (for example ethanol). The ratio of the lipids has a mole percent range of 25-98 for the cationic lipid with a target of 35-65, the helper lipid has a mole percent range from 0-75 with a target of 30-50, the PEG lipid has a mole percent range from 1-15 with a target of 1-6, and the DSPC has a mole precept range of 0-15 with a target of 0-12. The siRNA solution contains one or more siRNA sequences at a concentration range from 0.3 to 1.0 mg/mL with a target of 0.3-0.9 mg/mL in a sodium citrate buffered salt solution with pH in the range of 3.5-5. The two liquids are heated to a temperature in the range of 15-40° C., targeting 30-40° C., and then mixed in an impinging jet mixer instantly forming the LNP. The teeID has a range from 0.25 to 1.0 mm and a total flow rate from 10-600 mL/min. The combination of flow rate and tubing ID has effect of controlling the particle size of the LNPs between 30 and 200 nm. The solution is then mixed with a buffered solution at a higher pH with a mixing ratio in the range of 1:1 to 1:3 vol:vol but targeting 1:2 vol:vol. This buffered solution is at a temperature in the range of 15-40° C., targeting 30-40° C. The mixed LNPs are held from 30 minutes to 2 hrs prior to an anion exchange filtration step. The temperature during incubating is in the range of 15-40° C., targeting 30-40° C. After incubating the solution is filtered through a 0.8 um filter containing an anion exchange separation step. This process uses tubing IDs ranging from 1 mm ID to 5 mm ID and a flow rate from 10 to 2000 mL/min. The LNPs are concentrated and diafiltered via an ultrafiltration process where the alcohol is removed and the citrate buffer is exchanged for the final buffer solution such as phosphate buffered saline. The ultrafiltration process uses a tangential flow filtration format (TFF). This process uses a membrane nominal molecular weight cutoff range from 30-500 KD. The membrane format can be hollow fiber or flat sheet cassette. The TFF processes with the proper molecular weight cutoff retains the LNP in the retentate and the filtrate or permeate contains the alcohol; citrate buffer; final buffer wastes. The TFF process is a multiple step process with an initial concentration to a siRNA concentration of 1-3 mg/mL. Following concentration, the LNPs solution is diafiltered against the final buffer for 10-20 volumes to remove the alcohol and perform buffer exchange. The material is then concentrated an additional 1-3 fold. The final steps of the LNP process are to sterile filter the concentrated LNP solution and vial the product.

Analytical Procedure:

1) siRNA Concentration

The siRNA duplex concentrations are determined by Strong Anion-Exchange High-Performance Liquid Chromatography (SAX-HPLC) using Waters 2695 Alliance system (Water Corporation, Milford Mass.) with a 2996 PDA detector. The LNPs, otherwise referred to as RNAi Delivery Vehicles (RDVs), are treated with 0.5% Triton X-100 to free total siRNA and analyzed by SAX separation using a Dionex BioLC DNAPac PA 200 (4×250 mm) column with UV detection at 254 nm. Mobile phase is composed of A: 25 mM $NaClO_4$, 10 mM Iris, 20% EtOH, pH 7.0 and B: 250 mM $NaClO_4$, 10 mM Iris, 20% EtOH, pH 7.0 with liner gradient from 0-15 min and flow rate of 1 ml/min. The siRNA amount is determined by comparing to the siRNA standard curve.

2) Encapsulation Rate

Fluorescence reagent SYBR Gold is employed for RNA quantitation to monitor the encapsulation rate of RDVs. RDVs with or without Triton X-100 are used to determine the free siRNA and total siRNA amount. The assay is performed using a SpectraMax M5e microplate spectrophotometer from Molecular Devices (Sunnyvale, Calif.). Samples are excited at 485 ran and fluorescence emission was measured at 530 nm. The siRNA amount is determined by comparing to the siRNA standard curve.

Encapsulation rate=(1−free siRNA/total siRNA)× 100%

3) Particle Size and Polydispersity

RDVs containing 1 μg siRNA are diluted to a final volume of 3 ml with 1×PBS. The particle size and polydispersity of the samples is measured by a dynamic light scattering method using ZetaPALS instrument (Brookhaven Instruments Corporation, Holtsville, N.Y.). The scattered intensity is measured with He—Ne laser at 25° C. with a scattering angle of 90°.

4) Zeta Potential Analysis

RDVs containing 1 μg siRNA are diluted to a final volume of 2 ml with 1 mM Tris buffer (pH 7.4). Electrophoretic mobility of samples is determined using ZetaPALS instrument (Brookhaven Instruments Corporation, Holtsville, N.Y.) with electrode and He—Ne laser as a light source. The Smoluchowski limit is assumed in the calculation of zeta potentials.

5) Lipid Analysis

Individual lipid concentrations are determined by Reverse Phase High-Performance Liquid Chromatography (RP-HPLC) using Waters 2695 Alliance system (Water Corporation, Milford Mass.) with a Corona charged aerosol detector (CAD) (ESA Biosciences, Inc, Chelmsford, Mass.). Individual lipids in RDVs are analyzed using an Agilent Zorbax SB-C18 (50×4.6 mm, 1.8 μm particle size) column with CAD at 60° C. The mobile phase is composed of A: 0.1% TFA in $H_2O$ and B: 0.1% TFA in IPA. The gradient changes from 60% mobile phase A and 40% mobile phase B from time 0 to 40% mobile phase A and 60% mobile phase B at 1.00 min; 40% mobile phase A and 60% mobile phase B from 1.00 to 5.00 min; 40% mobile phase A and 60% mobile phase B from 5.00 min to 25% mobile phase A and 75% mobile phase B at 10.00 min; 25% mobile phase A and 75% mobile phase B from 10.00 min to 5% mobile phase A and 95% mobile phase B at 15.00 min; and 5% mobile phase A and 95% mobile phase B from 15.00 to 60% mobile phase A and 40% mobile phase B at 20.00 mm with flow rate of 1 ml/min. The individual lipid concentration is determined by comparing to the standard curve with all the lipid components in the RDVs with a quadratic curve fit. The molar percentage of each lipid is calculated based on its molecular weight.

Utilizing the above described LNP process, specific LNPs with the following ratios were identified:

```
Nominal composition:

Cationic Lipid / Cholesterol / PEG-DMG 60/38/2
Cationic Lipid! Cholesterol / PEG-DMG 67.3/29/3.7
Luc siRNA 5'-iB-AUAAGGCUAUGAAGAGAUATT-iB 3' (SEQ.ID.NO.: 1)
       3'-UUUAUUCCGAUACUUCUCUAU-5' (SEQ.ID.NO.: 2)
                    AUGC — Ribose
                    iB — Inverted deoxy abasic
                        UC — 2' Fluoro
                        AGT — 2' Deoxy
                        AGU — 2' OCH3
Nominal composition Cationic Lipid /Cholesterol/PEG-DMG 60/38/2
Cationic Lipid / Cholesterol / PEG-DMG / DSPC 40/48/2/10
Cationic Lipid / Cholesterol / PEG-DMG / DSPC 58/30/2/10
ApoB siRNA 5'-iB-CUUUAACAAUUCCUGAAAUTT-iB (SEQ ID NO. : 3)
       3'-UUGAAAUUGUUAAGGACUUUA-5' (SEQ ID NO.: 4)
                    AUGC — Ribose
                    iB — Inverted deoxy abasic
                        UC — 2' Fluoro
                        AGT — 2' Deoxy
                        AGU — 2' OCH3
Nominal composition Cationic Lipid /Cholesterol/PEG-DMG 60/38/2
Cationic Lipid / Cholesterol / PEG-DMG / DSPC 40/48/2/10
Cationic Lipid / Cholesterol / PEG-DMG / DSPC 58/30/2/10
ApoB siRNA 5'-iB-CUUUAACAAUUCCUGAAAUTsT-iB-3' (SEQ ID NO. : 5)
       3'-UsUGAAAUUGUUAAGGACUsUsUsA-5' (SEQ ID NO. : 6)
                    AUGC — Ribose
                    iB — Inverted deoxy abasic
                        UC — 2' Fluoro
                        AGT — 2' Deoxy
                        AGU — 2' OCH3
                    AUGC — Ribose
```

The synthesis and use of oligonucleotides, in particular siRNA and miRNA, are known. (See US patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405 and WO2010/054406). See also Semple S. C. et al., Rational design of cationic lipids for siRNA delivery, Nature Biotechnology, published online 17 Jan. 2010; doi:10.1038/nbt.1602.

Example 1

Mouse In Vivo Evaluation of Efficacy

LNPs utilizing Compounds 1-2, in the nominal compositions described immediately above, were evaluated for in vivo efficacy and induction of inflammatory cytokines in a luciferase mouse model. The siRNA targets the mRNA transcript for the firefly (*Photinus pyralis*) luciferase gene (Accession #M15077). The primary sequence and chemical modification pattern of the luciferase siRNA is displayed above. The in vivo luciferase model employs a transgenic mouse in which the firefly luciferase coding sequence is present in all cells. ROSA26-LoxP-Stop-LoxP-Luc (LSL-Luc) transgenic mice licensed from the Dana Farber Cancer Institute are induced to express the Luciferase gene by first removing the LSL sequence with a recombinant Ad-Cre virus (Vector Biolabs). Due to the organo-tropic nature of the virus, expression is limited to the liver when delivered via tail vein injection. Luciferase expression levels in liver are quantitated by measuring light output, using an IVIS imager (Xenogen) following administration of the luciferin substrate (Caliper Life Sciences). Pre-dose luminescence levels are measured prior to administration of the RDVs. Luciferin in PBS (15 mg/mL) is intraperitoneally (IP) injected in a volume of 150 µL. After a four minute incubation period mice are anesthetized with isoflurane and placed in the IVIS imager. The RDVs (containing siRNA) in PBS vehicle were tail vein injected n a volume of 0.2 mL. Final dose levels ranged from 0.3 to 3 mg/kg siRNA. PBS vehicle alone was dosed as a control. Three hours post dose, mice were bled retro-orbitally to obtain plasma for cytokine analysis. Mice were imaged 48 hours post dose using the method described above. Changes in luciferin light output directly correlate with luciferase mRNA levels and represent an indirect measure of luciferase siRNA activity. In vivo efficacy results are expressed as % inhibition of luminescence relative to pre-dose luminescence levels. Plasma cytokine levels were determined using the SearchLight multiplexed cytokine chemiluminescent array (Pierce/Thermo). Systemic administration of the luciferase siRNA RDVs decreased luciferase expression in a dose dependant manner. Greater efficacy was observed in mice dosed with Compound 1 containing RDVs than with the RDV containing the octyl-CLinDMA (OCD) cationic lipid (FIG. 1). OCD is known and described in WO2010/021865.

Rat In Vivo Evaluation of Efficacy and Toxicity

Figure 2:
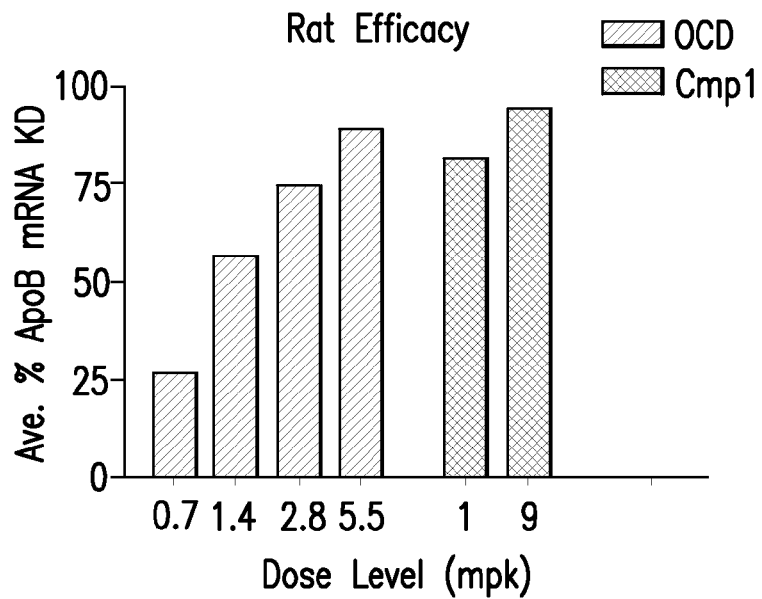
FIG. 2: LNP (Compound 1) efficacy in rat.
Figure 3:
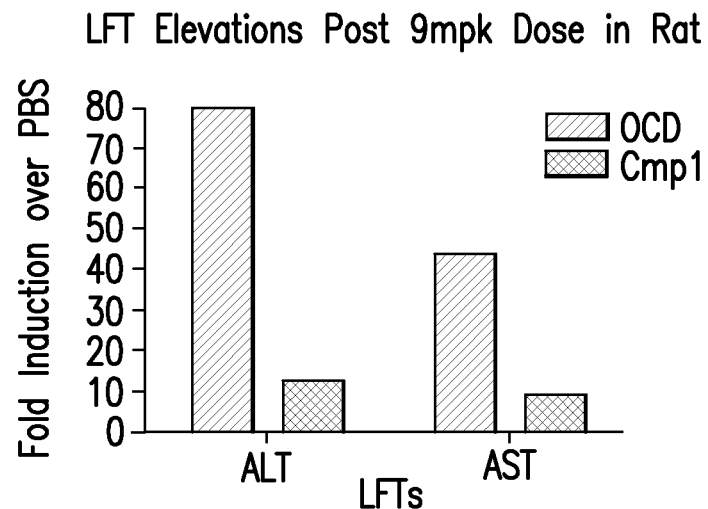
FIG. 3: LNP (Compound 1) LFT elevations in rat.

LNPs utilizing Compound 1 in the nominal compositions described above, were evaluated for in vivo efficacy and increases in alanine amino transferase and aspartate amino transferase in Sprague-Dawley (Crl:CD(SD) female rats (Charles River Labs). The siRNA targets the mRNA transcript for the ApoB gene (Accession # NM 019287). The primary sequence and chemical modification pattern of the ApoB siRNA is displayed above. The RDVs (containing siRNA) in PBS vehicle were tail vein injected in a volume of 1 to 1.5 mL. Infusion rate is approximately 3 ml/min. Five rats were used in each dosing group. After LNP administration, rats are placed in cages with normal diet and water present. Six hours post dose, food is removed from the cages. Animal necropsy is performed 24 hours after LNP dosing. Rats are anesthetized under isoflurane for 5 minutes, then maintained under anesthesia by placing them in nose cones continuing the delivery of isoflurane until ex-sanguination is completed. Blood is collected from the vena cava using a 23 gauge butterfly venipuncture set and aliquoted to serum separator vacutainers for serum chemistry analysis. Punches of the excised caudate liver lobe are taken and placed in RNALater (Ambion) for mRNA analysis. Preserved liver tissue was homogenized and total RNA isolated using a Qiagen bead mill and the Qiagen miRNA-Easy RNA isolation kit following the manufacturer's instructions. Liver ApoB mRNA levels were determined by quantitative RT-PCR. Message was amplified from purified RNA utilizing a rat ApoB commercial probe set (Applied Biosystems Cat # RN01499054_m1). The PCR reaction was performed on an ABI 7500 instrument with a 96-well Fast Block. The ApoB mRNA level is normalized to the housekeeping PPIB (NM 011149) mRNA. PPIB mRNA levels were determined by RT-PCR using a commercial probe set (Applied Biosystems Cat. No. Mm00478295_m1). Results are expressed as a ratio of ApoB mRNA/PPIB mRNA. All mRNA data is expressed relative to the PBS control dose. Serum ALT and AST analysis were performed on the Siemens Advia 1800 Clinical Chemistry Analyzer utilizing the Siemens alanine aminotransferase (Cat#03039631) and aspartate aminotransferase (Cat#03039631) reagents. Greater efficacy was observed in rats dosed with Compound 1 containing RDV than with the RDV containing the octyl-CLinDMA cationic lipid (FIG. 2). Additionally, lower elevations in LFTs (ALT/AST) were observed in rats dosed with Compound 1 containing RDV than with the RDV containing the octyl-CLinDMA cationic lipid (FIG. 3).

Determination of Cationic Lipid Levels in Rat Liver

Liver tissue was weighed into 20-ml vials and homogenized in 9 v/w of water using a GenoGrinder 2000 (OPS Diagnostics, 1600 strokes/min, 5 min). A 50 µL aliquot of each tissue homogenate was mixed with 300 µL of extraction/protein precipitating solvent (50/50 acetonitrile/methanol containing 500 nM internal standard) and the plate was centrifuged to sediment precipitated protein. A volume of 200 µL of each supernatant was then transferred to separate wells of a 96-well plate and 10 µl samples were directly analyzed by LC/MS-MS.

Standards were prepared by spiking known amounts of a methanol stock solution of Compound 1 or OCD into untreated rat liver homogenate (9 vol water/weight liver). Aliquots (50 µL) each standard/liver homogenate was mixed with 300 µL of extraction/protein precipitating solvent (50/50 acetonitrile/methanol containing 500 nM internal standard) and the plate was centrifuged to sediment precipitated protein. A volume of 200 µL of each supernatant was transferred to separate wells of a 96-well plate and 10 µl of each standard was directly analyzed by LC/MS-MS.

Figure 4:
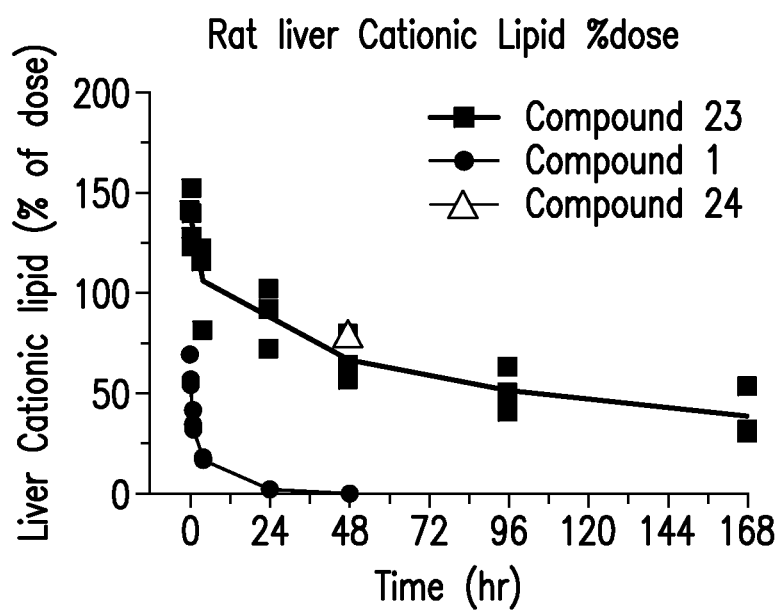
FIG. 4: Cationic lipid (Compound 1) liver levels in rat.

Absolute quantification versus standards prepared and extracted from rat liver homogenate was performed using an Aria LX-2 HPLC system (Thermo Scientific) coupled to an API 4000 triple quadrupole mass spectrometer (Applied Biosystems). For each run, a total of 10 µL sample was injected onto a BDS Hypersil C8 HPLC column (Thermo, 50×2 mm, 3 µm) at ambient temperature (FIG. 4).

Mobile Phase A: 95% H2O/5% methanol/10 mM ammonium formate/0.1% formic acid Mobile Phase B: 40% methanol/60% n-propanol/10 mM ammonium formate/0.1% formic acid The flow rate was 0.5 mL/min and gradient elution profile was as follows: hold at 80% A for 0.25 min, linear ramp to 100% B over 1.6 min, hold at 100%13 for 2.5 min, then return and hold at 80% A for 1.75 min. Total run time was 5.8 min. API 4000 source parameters were CAD: 4, CUR: 15, GS1: 65, GS2: 35, IS: 4000, TEM: 550, CXP: 15, DP: 60, EP: 10.

What is claimed is:

1. A cationic lipid of Formula A:

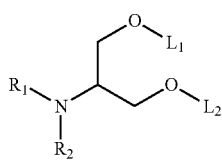

wherein:
$R^1$ and $R^2$ are independently selected from H, ($C_1$-$C_6$) alkyl, heterocyclyl, and polyamine, wherein said alkyl, heterocyclyl and polyamine are optionally substituted with one to three substituents selected from R', or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one to three substituents selected from R';

R' is independently selected from halogen, R", OR", SR", CN, $CO_2$R" or CON(R")$_2$;

R" is independently selected from H and $(C_1-C_6)$alkyl, wherein said alkyl is optionally substituted with halogen and OH;

$L_1$ is selected from

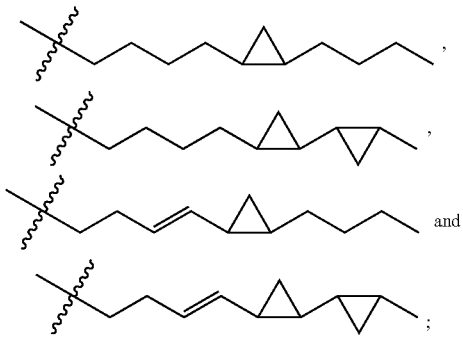

and $L_2$ is selected from $C_3-C_{13}$ alkyl and $C_3-C_{13}$ alkenyl, said alkyl and alkenyl are optionally substituted with one or more substituents selected from R';

or any pharmaceutically acceptable salt or stereoisomer thereof.

2. A cationic lipid according to claim 1, wherein:

$R^1$ and $R^2$ are each methyl;

$L_1$ is selected from

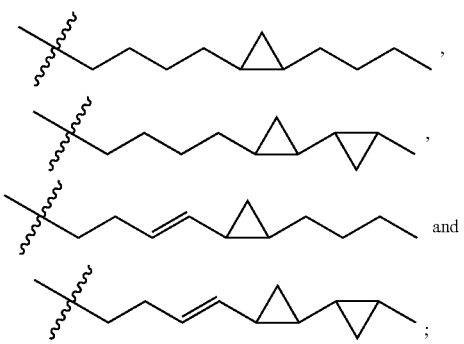

and $L_2$ is selected from $C_3-C_{13}$ alkyl and $C_3-C_{13}$ alkenyl;

or any pharmaceutically acceptable salt or stereoisomer thereof.

3. A lipid nanoparticle comprising a cationic lipid of claim 1.

4. The lipid nanoparticle of claim 3, wherein the lipid nanoparticle comprises oligonucleotides.

5. The lipid nanoparticle of claim 4, wherein the oligonucleotide are siRNA or miRNA.

6. The lipid nanoparticle of claim 4 wherein the oligonucleotide are siRNA.

* * * * *